(12) United States Patent
Gall et al.

(10) Patent No.: US 8,291,537 B2
(45) Date of Patent: Oct. 23, 2012

(54) ORAL HYGIENE DEVICE AND METHOD OF ASSEMBLY

(75) Inventors: Douglas A. Gall, Strongsville, OH (US);
Craig Saunders, Rocky River, OH (US);
John W. Spirk, Gates Mills, OH (US);
John R. Nottingham, Bratenahl, OH (US)

(73) Assignee: Nottingham-Spirk Design Associates, Inc., Cleveland, OH (US)

( * ) Notice: Subject to any disclaimer, the term of this patent is extended or adjusted under 35 U.S.C. 154(b) by 883 days.

(21) Appl. No.: 11/972,252

(22) Filed: Jan. 10, 2008

(65) Prior Publication Data

US 2009/0178215 A1    Jul. 16, 2009

(51) Int. Cl.
*A46B 13/00* (2006.01)

(52) U.S. Cl. ............... 15/22.1; 15/21.1; 15/22.4; 15/23; 15/24; 15/28; 15/29

(58) Field of Classification Search ............. 15/22.1, 15/22.2, 22.4, 21.1, 23, 24, 28, 29
See application file for complete search history.

(56) References Cited

U.S. PATENT DOCUMENTS

| | | | |
|---|---|---|---|
| 2,917,758 A | 12/1959 | Held et al. | |
| 3,183,538 A | 5/1965 | Hübner | |
| 3,278,963 A | 10/1966 | Bond | |
| 3,538,530 A | 11/1970 | Stemme | |
| 4,326,314 A * | 4/1982 | Moret et al. | 15/22.1 |
| 5,214,819 A | 6/1993 | Kirchner | |
| 5,311,633 A | 5/1994 | Herzog et al. | |
| 5,378,153 A | 1/1995 | Giuliani et al. | |
| 5,504,958 A | 4/1996 | Herzog | |
| 5,577,285 A | 11/1996 | Drössler | |
| RE35,712 E | 1/1998 | Murayama | |
| 5,850,655 A | 12/1998 | Göcking et al. | |
| 5,934,908 A | 8/1999 | Woog et al. | |
| 5,974,615 A | 11/1999 | Schwarz-Hartmann et al. | |
| 6,140,723 A | 10/2000 | Matsui et al. | |
| 6,195,828 B1 | 3/2001 | Fritsch | |
| 6,308,359 B2 | 10/2001 | Fritsch et al. | |
| 6,363,565 B1 | 4/2002 | Paffrath | |
| 7,067,945 B2 * | 6/2006 | Grez et al. | 310/50 |
| 7,162,764 B2 | 1/2007 | Drössler et al. | |
| 2003/0154567 A1 | 8/2003 | Drössler et al. | |

FOREIGN PATENT DOCUMENTS

| | | |
|---|---|---|
| FR | 1.299.056 | 6/1962 |
| GB | 899618 | 6/1962 |
| GB | 1134158 | 11/1966 |
| GB | 1134158 | 5/1967 |
| WO | WO 02/054906 A1 | 7/2002 |

* cited by examiner

*Primary Examiner* — Robert Scruggs
(74) *Attorney, Agent, or Firm* — Fay Sharpe LLP

(57) ABSTRACT

An oral hygiene device includes a handle and a cleaning head supported on one end of the handle. A vibratory source is supported on the handle and is operative to generate vibratory output. A mounting element is disposed between the handle and the vibratory source. A connecting member extends between the vibratory source and the cleaning head, and is adapted to generate motion at the cleaning head in response to the vibratory output generated at the vibratory source.

21 Claims, 5 Drawing Sheets

ORAL HYGIENE DEVICE AND METHOD OF ASSEMBLY

BACKGROUND

The subject matter of the present disclosure broadly relates to the art of oral hygiene devices.

BRIEF DESCRIPTION

A wide variety of types and kinds of oral hygiene devices have been developed that include one or more displaceable elements and/or components for use in performing hygienic actions, such as the brushing or flossing of teeth, for example. Typically, the one or more displaceable elements and/or components are driven by an electrically powered device. In some cases, the elements and/or components are driven by a linear actuator, such as a piezoelectric transducer, for example. In other cases, the elements and/or components can be driven by a rotational output shaft of an electric motor. In either case, certain disadvantages exist with regard to known constructions that may undesirably influence the performance of such known oral hygiene devices and/or manufacturing costs associated therewith.

As one example, some oral hygiene devices are known to utilize one or more linear actuators or transducers to displace the head assembly, and/or components or elements thereof, in one or more directions. Commonly, a piezoelectric transducer will be used to vibrate the head assembly, and/or components or elements thereof, at high frequency. One disadvantage of such constructions, however, is that complex and expensive electronics are often used to power the one or more actuators and thereby control the movement and operation of the hygienic elements and/or components, which movement is often a complex or random oscillating motion.

Additionally, linear transducers used in known oral hygiene devices are often capable of only limited displacement and/or output force. As such, these actuators are commonly mounted in proximal relation to the hygienic elements and/or components that are driven thereby, such as within the head assembly or toward a distal end of an elongated neck of an oral hygiene device, for example, to minimize mechanical and other losses. However, these portions or areas of an oral hygiene device often provide only a limited envelope within which to mount the actuators. As such, space constraints can operate to further limit the size and/or performance characteristics of the linear actuators and/or transducers that may be used in these known oral hygiene devices.

In other cases, some known oral hygiene devices utilize the output from rotary actuators, typically electric motors, to generate displacement at the head assembly, and/or elements or components thereof, in one or more directions. Typically, these constructions utilize one or more components to mechanically convert continuous rotary motion output by the rotary actuator into a linear and/or rotational oscillating motion. Generally, such constructions are capable of generating increased stroke and output forces compared to previously described oral hygiene devices. However, due to the sliding of the various mechanical components of the transmission relative to one another, issues such as part wear and reduced performance can occur. Additionally, the frictional forces associated with this sliding motion can also result in a decrease in performance, in some cases.

Accordingly, it is believed desirable to develop oral hygiene devices that overcome one or more of the foregoing and/or other difficulties associated with constructions of known oral hygiene devices.

BRIEF SUMMARY

A toothbrush according to the subject matter of the present disclosure is provided that includes a handle including a handle wall that at least partially defines a handle cavity. The handle extends longitudinally between spaced first and second ends. A vibratory source is disposed within the handle cavity in longitudinally-spaced relation to the first end of the handle. The vibratory source is adapted to undergo vibratory movement and thereby generate vibratory output. A mounting element is supported on the handle within the handle cavity and in longitudinally-spaced relation to the first end of the handle. The mounting element includes an outer mounting wall that is adapted to engage the handle wall. The mounting element also includes an inner mounting wall that is adapted to receive the vibratory source. The mounting element further includes at least one intermediate wall suspending the inner mounting wall from the outer mounting wall such that the vibratory source can undergo vibratory movement within the handle cavity and thereby generate vibratory output. A connecting member extends longitudinally between opposing first and second member ends. The first member end is fixedly connected to the vibratory source such that the connecting member projects from the vibratory source toward the first end of the handle. A bearing surface is disposed along the handle within the handle cavity and is spaced from the vibratory source toward the first end of the handle. The connecting member engages the bearing surface such that vibratory output from the vibratory source, when acting in a first direction, results in vibratory output at the second end of the connecting member acting in an opposing second direction. A cleaning head is received along the first end of the handle and operatively interengages the second end of the connecting member such that the vibratory output at the second end of the connecting member is communicated to the cleaning head and the cleaning head is thereby displaced in the opposing second direction.

An oral hygiene device in accordance with the subject matter of the present disclosure is provided that includes a handle including a handle wall at least partially defining a handle chamber. The handle including a proximal end and a distal end that is spaced longitudinally from the proximal end. A cleaning head is supported for vibratory movement on the distal end of the handle. A vibratory source is supported on the handle within the handle chamber and in spaced relation to the distal end. The vibratory source is operative to generate vibratory output. A mounting member is disposed within the handle chamber between the vibratory source and the handle wall such that the vibratory source is suspended by the mounting member within the handle chamber and is thereby capable of undergoing vibratory displacement resulting in the vibratory output. A connecting member is operatively connected between the vibratory source and the cleaning head. A bearing surface is provided along one of the handle and the cleaning head. The bearing surface is adapted to permit the cleaning head to move relative to the handle and thereby generate motion in the cleaning head in response to the vibratory output of the vibratory source.

A method of assembling an oral hygiene device in accordance with the subject matter of the present disclosure is provided that includes providing a handle that includes a handle wall at least partially defining a handle cavity. The handle extending longitudinally between proximal and distal handle ends. The method also includes providing a vibratory source and supporting the vibratory source within the handle cavity in spaced relation to the distal end such that the vibratory source generates vibratory output along a principal plane of motion. The method further includes providing a bearing surface on the handle between the vibratory source and the distal end of the handle. The method also includes providing a connecting member that extends longitudinally between first and second ends thereof. The method further includes supporting the connecting member along the bearing surface and operatively interconnecting the first end of the connecting member with the vibratory source. The method also includes providing a cleaning head and operatively interconnecting the cleaning head and the second end of the connecting member such that the connecting member can pivot about the bearing surface in response to the vibratory output from the vibratory source and thereby generate corresponding vibratory output at the cleaning head.

DETAILED DESCRIPTION

Figure 1:
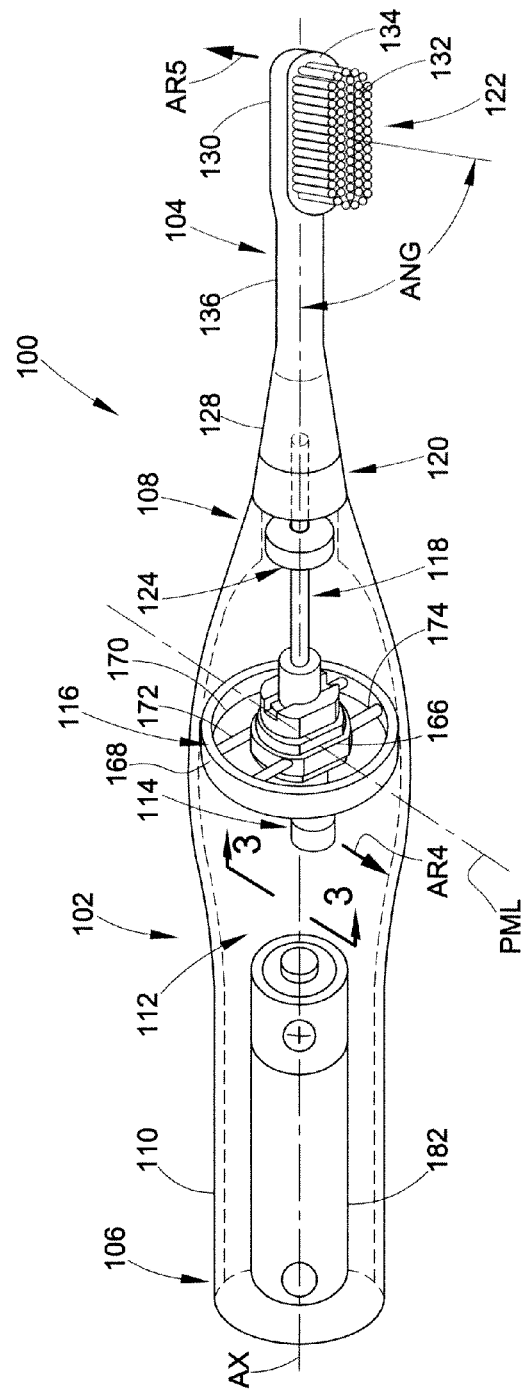
FIG. 1 is perspective view, in partial cross section, of an exemplary oral hygiene device in accordance with the subject matter of the present disclosure.

Turning now to the drawings, wherein the showings are for the purpose of illustrating examples of the subject matter of the present disclosure and which showings are not intended as limitations of the same, FIG. 1 illustrates an exemplary oral hygiene device 100 that includes a handle 102 and a cleaning head 104 that is movably supported on the handle. While it will be appreciated that an oral hygiene device in accordance with the subject matter of the present disclosure can be of any suitable size, shape, form, configuration and/or construction, handle 102 of oral hygiene device 100 is shown in FIG. 1 as including a longitudinal axis AX and extending longitudinally between a first or proximal handle end 106 and an opposing, second or distal handle end 108. Handle 102 is also shown as including a handle wall 110 that at least partially defines a handle cavity 112.

Additionally, an oral hygiene device in accordance with the subject matter of the present disclosure will include a vibratory source adapted to generate vibratory output, which can, in turn, be transmitted to the cleaning head for movement thereof relative to the handle. In the example shown in FIGS. 1 and 2, oral hygiene device 100 includes a vibratory source 114 that is supported on handle 102 and is operative to generate vibratory output. In the exemplary arrangement shown, vibratory source 114 is disposed within handle cavity 112 and is supported therein such that the vibratory source is capable of undergoing vibratory displacement relative to handle 102, though it will be recognized that any other suitable arrangement could alternately be used. Furthermore, the vibratory source (e.g., vibratory source 114) can be supported on, in or along the handle (e.g., handle 102) in any suitable manner and/or by using any suitable mounting elements or components. In the exemplary case shown in FIGS. 1 and 2, vibratory source 114 is suspended within handle cavity 112 by a mounting member 116 that is disposed between handle wall 110 and the vibratory source. However, it will be appreciated that any number of one or more mounting elements or other components could alternately be used.

Figure 2:
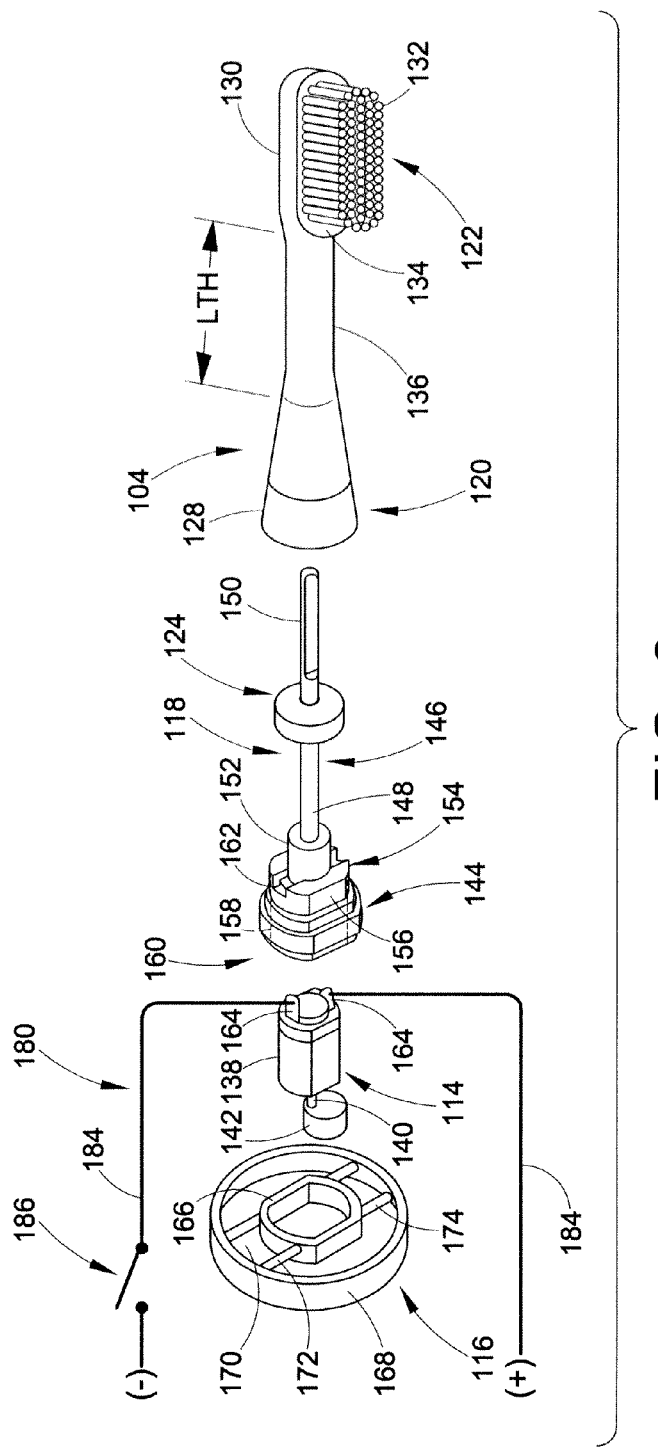
FIG. 2 is an exploded perspective view of a portion of the exemplary oral hygiene device in FIG. 1.
Figure 3:
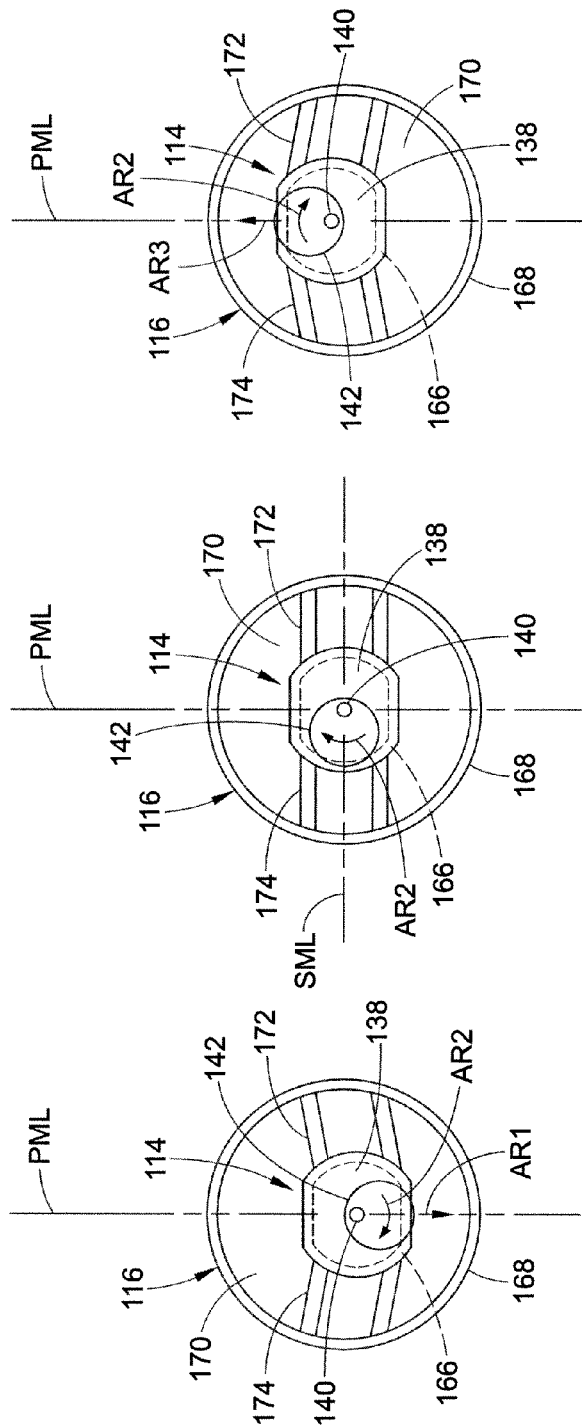
FIGS. 3A-C are end views of the exemplary vibratory source and support member in FIGS. 1 and 2 taken from line 3-3 in FIG. 1.

An oral hygiene device according to the subject matter of the present disclosure will also include a vibratory-output transfer member or assembly that is operatively connected between the vibratory source and the cleaning head. Such a member or assembly, which will also be referred to herein as a connector assembly, being capable of transmitting or otherwise transferring vibratory output from the vibratory source to the cleaning head and thereby generating vibratory motion at or along at least a portion of the cleaning head. Oral hygiene device 100 is also shown in FIGS. 1 and 2 as including a connector assembly 118 that is operatively disposed between vibratory source 114 and cleaning head 104. Connector assembly 118 is adapted to transfer, transmit or otherwise communicate vibratory output from vibratory source 114 to cleaning head 104 and can do so in any manner capable of generating movement of cleaning head 104 relative to handle 102. As such, it will be appreciated that cleaning head 104 can be supported on handle 102 in any suitable manner that permits movement thereof relative to the handle. What's more, cleaning head 104 could, optionally, be removably supported on or otherwise secured to handle 102 (or another component of the oral hygiene device) such that the cleaning head could be replaced and/or cleaning heads of different types and/or kinds could alternately be used.

As one example, the handle and cleaning head could each include a bearing surface (not shown) with the cleaning head secured on the handle such that the bearing surfaces thereof are in abutting engagement with one another. In this manner, the bearing surface of the cleaning head could pivot, oscillate or otherwise move relative to the bearing surface of the handle. This, in turn, would permit the cleaning head to move relative to the handle, such as under the influence of vibratory output from the vibratory source communicated to the cleaning head by way of the connecting member, for example. A suitable seal (not shown) could optionally be provided between the handle and the cleaning head to prevent the ingress of water and/or other substances into the handle cavity and/or other portions of the handle and/or cleaning head.

As another example, cleaning head 104 could include a first or proximal head end 120 and an opposing, second or distal head end 122 disposed in longitudinally-spaced relation to the first head end. The cleaning head can be supported or otherwise secured on handle 104 such that first head end 120 is disposed toward second handle end 108 but spaced a distance therefrom, rather than being in abutting engagement therewith. In such case, a suitable seal (not shown) can optionally be provided between the handle and cleaning head, as has been discussed above. Additionally, to permit the cleaning head to pivot, oscillate, vibrate or otherwise move relative to the handle, a bearing surface can be disposed along the handle and/or otherwise provided in spaced relation to cleaning head 104.

Figure 4:
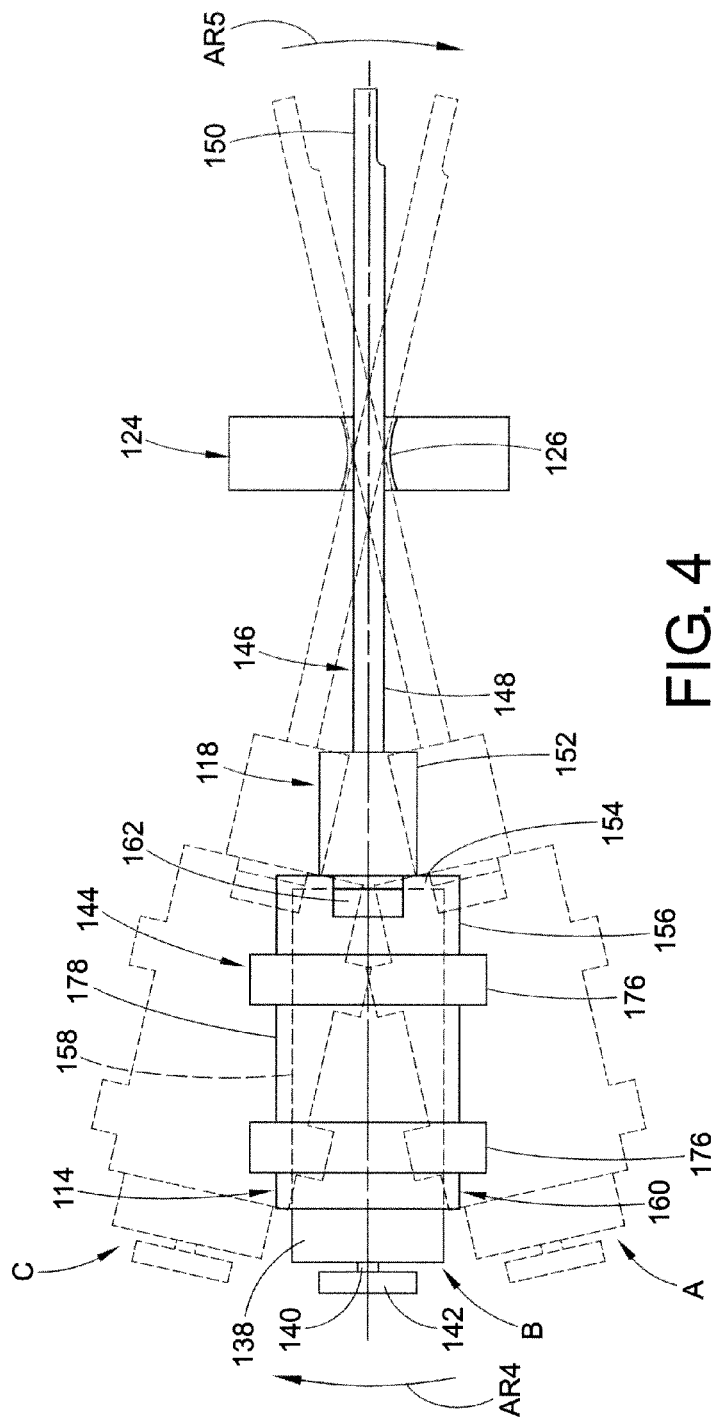
FIG. 4 is a side view of the exemplary vibratory source, connector assembly and bearing in FIGS. 1 and 2.

It will be appreciated that such a bearing surface can be provided in any suitable manner on or along any one or more features, elements and/or components of oral hygiene device 100 (e.g., handle wall 110), and can be of any suitable size, shape, construction and/or configuration. For example, the bearing surface could be integrally formed on or along the handle. As another example, a bearing element 124 could be supported on handle 102, such as along handle wall 110 and/or within handle cavity 112, for example. Bearing element 124 can then include a bearing surface 126 (FIG. 4) that at least partially defines a passage (not numbered) through the bearing element. Further to this example, one or more elements, components or features of connector assembly 118 can extend through the passage and engage bearing surface 126 of bearing element 124, such as is shown in FIGS. 1, 2 and 4.

The cleaning head of an oral hygiene device according to the subject matter of the present disclosure can be of any suitable type, kind, arrangement and/or construction, such as a cleaning head with one or more bristles (e.g., toothbrush heads) or a cleaning head that include a length of floss, a pick or another instrument, for example. As such, it will also be recognized that different cleaning heads may benefit from different types of motion, directions of movement and/or magnitudes of displacement. Accordingly, it will be understood that the performance, output and other operational characteristics of the vibratory source and/or the construction, arrangement and/or orientation of any one or more other features and/or components (e.g., mounting members, connector assemblies and bearing elements) can differ from application to application.

In the exemplary arrangement shown, cleaning head 104 includes a connection portion 128 disposed toward first head end 120 that is adapted to receive or otherwise operatively engage connector assembly 118. A head portion 130 is disposed in spaced relation to connection portion 128 and includes a plurality of bristles 132 disposed therealong. It will be appreciated that bristles 132 can extend or otherwise project from head portion 130 in any suitable manner and in any suitable configuration and/or alignment, such as having at least a portion of the plurality of bristles projecting from head portion 130 at an angle ANG of from about 10 degrees to about 90 degrees with respect to longitudinal axis AX. In the exemplary arrangement shown in FIGS. 1 and 2, plurality of bristles 132 extend from a head surface 134 in an approximately perpendicular orientation relative to longitudinal axis AX. Cleaning head 104 can also optionally include an elongated neck portion 136 extending between connection portion 128 and head portion 130. If provided, elongated neck portion 136 can be of any suitable size, shape, length and/or configuration such as may be desired for aesthetic, performance or other reasons. For example, elongated neck portion 136, if included, can have a reduced cross-section to enhance ergonomic and/or comfort factors associated with use of the oral hygiene device. As another example, elongated neck portion 136 is shown in FIG. 1 as having a length represented by dimension LTH (FIG. 2). It will be appreciated that such length could vary from cleaning head-to-cleaning head to thereby provide optimized performance or output characteristics of the cleaning element (e.g., bristles, floss, pick) of the cleaning head.

Additionally, or in the alternative, one or more output or performance characteristics of the vibratory source of the oral hygiene device could, optionally, be varied to provide the desired operational performance of the cleaning element of the cleaning head. However, such additional features and/or operations might, in some cases, result in undesirable increases manufacturing and other costs. As another alternative, vibratory source 114 can include a rotary actuator, such as an electric motor 138, for example, that includes a rotational output shaft 140 operable at a predetermined and approximately constant rotational speed. It will be appreciated that rotational output shaft 140 can be a direct drive output shaft from electric motor 138 or, alternately, can be an output shaft from a suitable gear set or transmission, such as a planetary gear set (not shown), for example. Thus, it will be appreciated that the rotary actuator can generate any suitable rotational output speed, such as a rotational speed within a range of from about 50 RPM to about 50,000 RPM, for example.

A vibratory mass 142 is shown as being operatively connected to output shaft 140. It will be appreciated that the vibratory mass can be secured to the rotational output shaft in a manner suitable. As one example, vibratory mass 142 can be eccentrically attached to output shaft 140, such as by using a threaded or crimped connection (not shown), for example. It will be appreciated that vibratory mass 142 can be of any suitable shape, size, configuration and/or construction. As such, the distance that the center of gravity of the vibratory mass is offset from the attachment point thereof to output shaft 140 will vary from application-to-application depending upon the desired output and performance of vibratory source 114.

In operation, vibratory source 114 generates vibratory output by energizing the rotary actuator (e.g., electric motor 138) and thereby rotating the output shaft thereof (e.g., rotational output shaft 140). Such rotation of the output shaft causes the vibratory mass (e.g., vibratory mass 142) to rotate about the central axis (not shown) of the output shaft. This rotation of the vibratory mass results in an unbalanced loading of the rotary actuator, which unbalanced loading can be utilized as vibratory output.

Vibratory source 114 is supported within handle cavity 112 such that rotational output shaft 140 and vibratory mass 142 thereof are disposed toward first handle end 106. As discussed above, vibratory source 114 is operatively connected to cleaning head 104 through connector assembly 118. As mentioned above, connector assembly 118 can be of any suitable size, shape, arrangement and/or construction. As shown in FIGS. 1, 2 and 4, connector assembly 118 includes a connector housing 144 and an elongated connector rod 146 that extends from the connector housing. Connector rod 146 includes a first or proximal end 148 disposed toward connector housing 144 and a second or distal end 150 disposed generally opposite connector housing 144. The second end of the connector rod can include any suitable features and/or elements for engaging cleaning head 104 such that vibratory output can be transmitted thereto from the vibratory source.

In one exemplary arrangement, connector rod 146 can be substantially fixedly attached to connector housing 144. In such case, vibratory output from vibratory source 114 can be transmitted to cleaning head 104 with minimal losses during transmission. In other cases, however, a more compliant interconnection between the connector housing and connector rod could be used, such as to generate less vibratory output at the cleaning head, for example.

It will be appreciated that connector housing 144 can be of any shape, size, construction, arrangement and/or configuration suitable for supporting vibratory source 114 and transmitting or otherwise transferring vibratory output from the vibratory source to the cleaning head. In the exemplary arrangement shown, connector housing 144 includes a longitudinally-extending post portion 152 disposed along a closed end 154 of the connector housing. Additionally, housing wall 156 is shown as at least partially defining a housing chamber 158 that includes an open end 160 generally opposite closed end 154. In one case, housing chamber 158 can be dimensioned to receive at least a portion of the rotary actuator (e.g., electric motor 138). One or more openings 162 can optionally be provided in connector housing 144, such as to receive or otherwise permit the passage of electrical terminals 164 through a wall (e.g., housing wall 156 and closed end 154) of the connector housing. Additionally, the rotary actuator can be secured in, on or along connector housing 144 in any suitable manner, such as by using mechanical fasteners (e.g., threaded fasteners, mounting clips), adhesive materials and/or overmolding techniques, for example.

Vibratory source 114 can be supported in, on or along handle 102 in any suitable manner. As one example, the vibratory source could be supported on the handle wall by a suitable mounting member or other support element. As another example, vibratory source 114 can be indirectly supported by mounting member 116, as is shown in FIGS. 1, 3A-C and 4. That is, vibratory source 114 is shown as being supported on connector housing 144 of connector assembly 118, and the connector housing is then directly supported on or along handle 102 by mounting member 116.

It will be appreciated that mounting member 116 can be of any size, shape, arrangement, configuration and/or construction suitable for supporting the vibratory source in, on or along the handle such that vibratory output can be generated by the vibratory source and transmitted to the cleaning head of the oral hygiene device. In the exemplary arrangement shown in FIGS. 1-4, mounting member 116 includes an inner wall 166 at least partially defining an inner opening (not numbered), an outer wall 168 at least partially defining an outer opening 170, and one or more walls or wall portions interconnecting the inner and outer walls. In the exemplary arrangement shown, mounting member 116 includes four intermediate walls 172 and 174 extending between and thereby interconnecting inner and outer walls 166 and 168. Intermediate walls 172 and 174 as shown as being disposed on opposing sides of a principal plane (or midplane) extending longitudinally through principal motion line PML. However, it will be appreciated that any other number, construction, arrangement and/or configuration interconnecting walls (e.g., intermediate walls 172 and 174) could alternately be use.

In the exemplary arrangement shown, connector housing 144 includes opposing flat sides (not numbered) as well as opposing curved sides (not numbered) which together form the outer periphery of the connector housing. Additionally, ribs or projecting wall portions 176 (FIG. 4) are disposed in spaced relation to one another. The projecting wall portions extend about the periphery of the connector housing forming a channel 178 (FIG. 4) therebetween. Inner wall 166 of mounting member 116 is received on or along connector housing 144 such that the inner wall is disposed at least partially within channel 178 and extends about housing wall 156 to at least partially secure the mounting member and connector assembly together.

Outer wall 168 of mounting member 116 is shown as being supported on or along handle wall 110 within handle cavity 112. However, it will be appreciated that any other mounting arrangement could alternately be used. In the exemplary arrangement shown, outer wall 168 at least partially defines outer opening 170 and is shown as being disposed in abutting engagement with handle wall 110. Intermediate walls 172 and 174 extend between the inner and outer walls and thereby bridge outer opening 170 to effectively suspend or otherwise minimally support vibratory source 114 within handle cavity 112. Though it will be appreciated that the vibratory source can be disposed in any suitable position along longitudinal axis AX, in the exemplary arrangement shown, at least a portion of vibratory source 114 is longitudinally positioned within the mounting member, such as within the axial extent of outer wall 168, for example.

It will be recognized that the arrangement, configuration and/or construction of one or more interconnecting walls (e.g., intermediate walls 172 and 174) can permit movement of inner wall 166 relative to outer wall 168 in one or more directions to a greater or lesser extent than in one or more other directions. In the exemplary embodiment shown, intermediate walls 172 and 174 permit inner wall 166 to move relative to outer wall 168 by approximately the same amount the opposing longitudinal directions (e.g., toward proximal end 106 and toward distal end 108). However, it will be recognized that intermediate walls 172 and 174 will also permit inner wall 166 to move relative to outer wall 168 along the direction of primary motion line PML by a greater amount than in the direction approximately transverse to the primary motion line.

Such biased directional movement can be attributed, at least in part, to the intermediate walls being capable of flexure or bending in the direction of the principal motion line in an amount that is substantially greater than the amount of compression/extension of those same intermediate walls in the direction transverse to the principal motion line, under the same load conditions. In one exemplary arrangement, such biased directional movement can include movement of about 25 percent or less in a direction approximately transverse to the principal motion line in comparison to the movement along the principal motion line under the same load conditions (e.g., under the out-of-balance load conditions generated by vibratory source 114).

One exemplary arrangement is illustrated in FIGS. 3A-C in which vibratory mass 142 is shown rotating about a point of rotation (e.g., a centerline of rotational output shaft 140) of the rotary actuator (e.g., electric motor 138). As shown in FIG. 3A, vibratory mass 142 is disposed in a first position in which the vibratory source is displaced along principal motion line PML, as indicated by arrow AR1, due, at least in part, to the flexing of intermediate walls 172 and 174 under the influence of the unbalanced load of the vibratory mass. As vibratory mass 142 rotates clockwise, as indicated by arrows AR2, the unbalanced load thereof is less effective at displacing the vibratory source due, at least in part, to the increased force required to compress and elongate the intermediate walls, as is represented in FIG. 3B. As such, substantially less displacement of vibratory source 114 occurs in the direction of a secondary motion line SML which is disposed approximately transverse to principal motion line PML. As one example, such displacement along secondary motion line SML can be less than 25 percent of the displacement along principal motion line PML. Additionally, as one example of such an arrangement, secondary motion line SML can be disposed perpendicular to principal motion line PML. As vibratory mass 142 continues to rotate clockwise, such as is shown in FIG. 3C, the unbalanced load condition induced by the vibratory mass, again, causes displacement along the principal motion line, as indicated by arrow AR3, due, at least in part, to the flexing of intermediate walls 172 and 174.

It will be recognized that arrows AR1 and AR3 extend along principal motion line PML but in generally opposite directions. As such, it will be appreciated that displacement of the vibratory source with respect to a longitudinally-extending plane formed through principal motion line PML may be of an approximately oscillating nature, as indicated by arrows AR4 and AR5 (FIGS. 1 and 4). Such oscillating motion is illustrated in FIG. 4 in which positions "A", "B" and "C" generally correspond to the operation and position of the components in FIGS. 3A, 3B and 3C, respectively. However, it will also be recognized that at least some amount of displacement will also occur in other, out-of-plane directions, such as along secondary motion line SML, for example. As such, vibratory source 114 may, in practice, move along an elongated, elliptical pathway. As one example, such an elongated elliptical pathway may include a minor axis having a length of 25 percent or less than the length of the major axis.

Returning to FIG. 4, vibratory source 114 and connector assembly 118 are shown pivoting along or about bearing surface 126 of bearing 124. As such, displacement of vibratory source 114 in one direction results in displacement of distal end 150 of elongated connector rod 146 in the opposing direction, as indicated by arrows AR4 and AR5.

One advantage of utilizing an arrangement capable of providing biased directional movement, such as has been described in detail above, is that the principal direction of vibratory output can be varied relative to the handle, simply by rotating the mounting member (e.g., mounting member 116) relative to the handle.

The vibratory source of an oral hygiene device in accordance with the subject matter of the present disclosure can be powered or otherwise operated in any suitable manner and by utilizing any suitable power source, such as electrical power, for example. In the exemplary arrangement shown, oral hygiene device 100 includes an electrical control system 180 that utilizes an electrical power supply, such as a battery 182 or an AC power adapter (not shown), for example. The electrical contacts of the electrical power supply can be in electrical communication with electrical terminals 164 of electric motor 138 in any suitable manner, such as by way of electrical leads 184, for example. Additionally, a switch 186 or other suitable device can be placed in electrical communication between the electrical power supply and the electric motor for selectively energizing the same.

Figure 5:
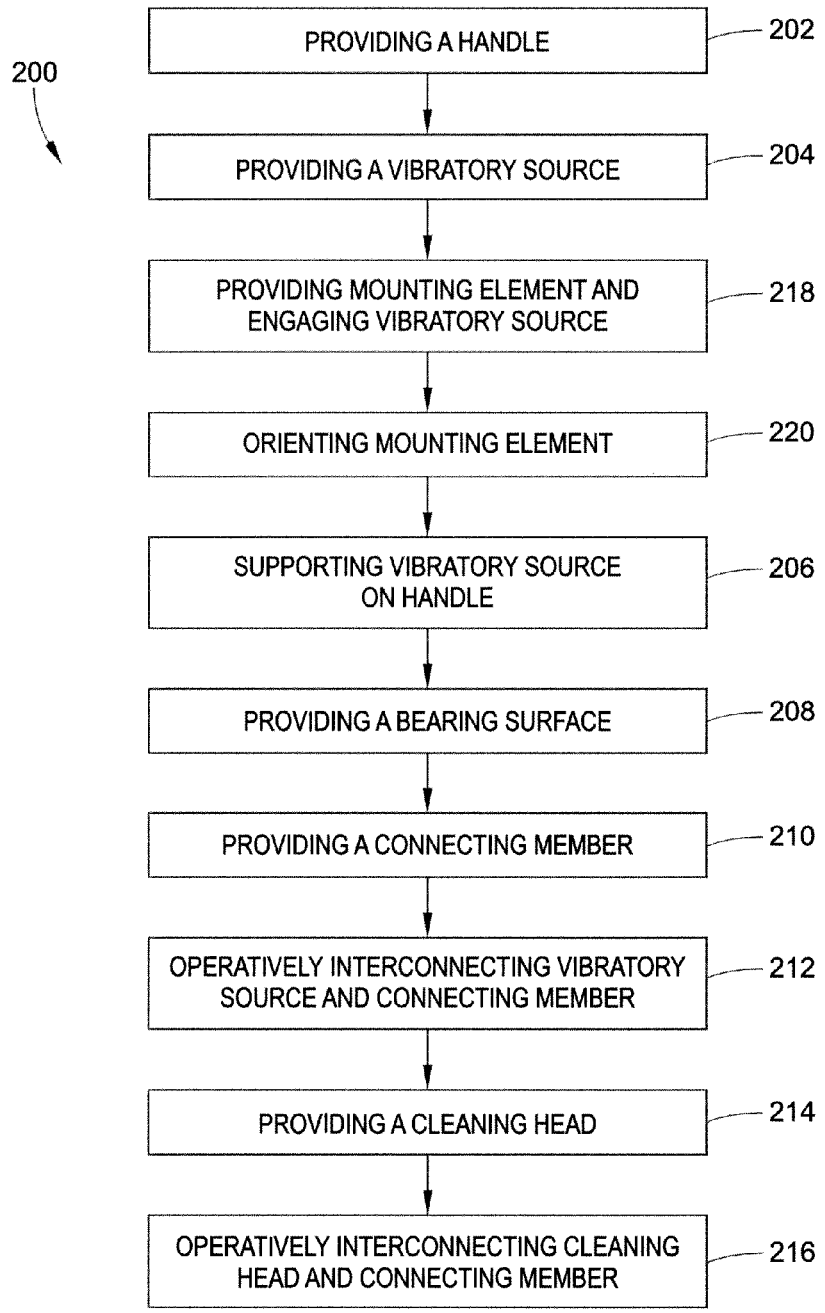
FIG. 5 is a flowchart representing one exemplary method of assembling an oral hygiene device in accordance with the subject matter of the present disclosure.

FIG. 5 illustrates one exemplary method 200 of assembling an oral hygiene device in accordance with the subject matter of the present disclosure, such as oral hygiene device 100, for example. Method 200 includes providing a handle, such as handle 102, for example, and providing a vibratory source, such as vibratory source 114, for example, as is indicated in FIG. 5 by boxes 202 and 204, respectively. Method 200 also includes supporting the vibratory source on the handle, as is represented by box 206. Method 200 can further include providing a bearing surface on the handle, as indicated in FIG. 5 by box 208. Method 200 also includes providing a connecting member, such as one or more components of connector assembly 118, for example, as is represented by box 210. Method 200 further includes operatively connecting the vibratory source and the connecting member, as is indicated in box 212 of FIG. 5. Method 200 also includes providing a cleaning head, such as cleaning head 104, for example, and operatively connecting the cleaning head and connecting member, as is represented in FIG. 5 by boxes 214 and 216.

Method 200 can optionally include providing a mounting element, such as at least a portion of mounting member 116, for example, and engaging at least a portion of the mounting element with the vibratory source, as is represented by box 218 in FIG. 5. Method 200 also optionally includes orienting the mounting element relative to at least one of either the vibratory source or the handle, as is indicated by box 220 in FIG. 5.

As used herein with reference to certain features, elements, components, structures, actions, operations and the like, numerical ordinals merely denote different singles of a plurality (e.g., "first handle end" and "second handle end," and "first intermediate wall" and "second intermediate wall") and do not imply any order or sequence unless specifically defined by the claim language.

While the subject novel concept has been described with reference to the foregoing embodiments and considerable emphasis has been placed herein on the structures and structural interrelationships between the component parts of the embodiments disclosed, it will be appreciated that other embodiments can be made and that many changes can be made in the embodiments illustrated and described without departing from the principles of the subject novel concept. Obviously, modifications and alterations will occur to others upon reading and understanding the preceding detailed description. Accordingly, it is to be distinctly understood that the foregoing descriptive matter is to be interpreted merely as illustrative of the present novel concept and not as a limitation. As such, it is intended that the subject novel concept be construed as including all such modifications and alterations insofar as they come within the scope of the appended claims and any equivalents thereof.

The invention claimed is:

1. A toothbrush comprising:
    a handle having a longitudinal axis and including a handle wall that extends around said axis and at least partially defines a handle cavity, said handle extending longitudinally between spaced first and second ends;
    a vibratory source disposed within said handle cavity in longitudinally-spaced relation to said first end of said handle;
    a mounting element disposed within said handle cavity and including an outer mounting wall supported along said handle wall, an inner mounting wall operatively engaging said vibratory source, and first and second intermediate walls having a length and extending between said inner and outer mounting walls in a lengthwise direction that is transverse to said axis such that flexing of said first and second intermediate walls along said length thereof permits movement of suspending said inner mounting wall and said vibratory source in a direction toward said outer mounting wall;
    a connecting member extending longitudinally between opposing first and second member ends, said first member end fixedly connected to said vibratory source such that said connecting member projects from along said vibratory source toward said first end of said handle;
    a bearing surface disposed along said handle and spaced from said vibratory source toward said first end of said handle, said connecting member engaging said bearing surface such that movement of said vibratory source in a first direction along a plane of motion results in movement at said second end of said connecting member in an opposing second direction along said plane of motion; and,
    a cleaning head received along said first end of said handle and operatively interengaging said second end of said connecting member such that said movement in said opposing second direction along said plane of motion at said second end of said connecting member is communicated to said cleaning head and said cleaning head is thereby displaced in said opposing second direction along said plane of motion.

2. A toothbrush according to claim 1, wherein said mounting element includes a midplane extending centrally through said inner and outer mounting walls in alignment with said axis, with said first and second intermediate walls disposed on opposing sides of said midplane such that said inner mounting wall is suspended therebetween.

3. A toothbrush according to claim 1, wherein said vibratory source includes a rotary actuator and a connector assembly operatively engaging said inner mounting wall and thereby supporting said rotary actuator within said handle cavity.

4. A toothbrush according to claim 3, wherein said rotary actuator includes a motor and said connector assembly includes a connector housing, said connector housing including a housing wall at least partially forming an open end and a closed end of said connector housing with a housing cavity formed into said connector housing from along said open end, said first end of said connecting rod being attached to said closed end of said connector housing, and said motor being at least partially received in said housing cavity.

5. A toothbrush according to claim 4, wherein said vibratory source includes an eccentrically-mounted vibratory mass that is disposed along said motor generally opposite said connector housing such that said vibratory mass is outwardly exposed from said connector housing and induces said movement of said inner mounting wall and said vibratory source during rotational operation of said motor.

6. A toothbrush according to claim 4 further comprising a pair of electrical contacts supported on said handle with said electrical contacts connected in electrical communication with said motor.

7. A toothbrush according to claim 6 further comprising a switch in electrical communication between said motor and one contact of said pair of contacts, said switch adapted to selectively place said motor and said one contact in electrical continuity with one another.

8. An oral hygiene device comprising:
   a handle including a longitudinal axis and a handle wall at least partially defining a handle chamber, said handle including a proximal end and a distal end that is spaced longitudinally from said proximal end;
   a cleaning head supported adjacent said distal end of said handle;
   a vibratory source disposed within said handle chamber and in spaced relation to said distal end, said vibratory source including a rotary actuator and a vibratory mass, said rotary actuator including a rotatable output shaft, and said vibratory mass eccentrically mounted on said rotatable output shaft;
   a mounting member disposed within said handle chamber and positioned between said vibratory source and said handle wall, said mounting member including an inner mounting wall, an outer mounting wall spaced radially outwardly from said inner mounting wall, and first and second intermediate walls extending lengthwise between and interconnecting said inner and outer mounting walls in a lengthwise direction that is transverse to said axis, said outer mounting wall abuttingly engaging said handle wall, said inner mounting wall operatively engaging said vibratory source such that said inner mounting wall and said vibratory source are suspended by said first and second intermediate walls within said handle chamber;
   a connecting member operatively connected between said vibratory source and said cleaning head; and,
   a bearing surface disposed adjacent said distal end of said handle and adapted to permit movement of said cleaning head relative to said handle;
   during use, rotation of said vibratory mass by said rotary actuator induces flexing along said length of said first and second intermediate walls thereby generating movement of at least said rotary actuator and said inner mounting wall in a direction toward said outer mounting wall and such that said movement of at least said rotary actuator and said inner mounting wall acting in a first direction along a plane of motion results in movement of said cleaning head in a second direction along said plane of motion that is opposite said first direction.

9. An oral hygiene device according to claim 8, wherein said bearing surface at least partially defines a bearing passage, and said connecting member extends through said bearing passage and pivots relative to said bearing surface within said bearing passage.

10. An oral hygiene device according to claim 8 further comprising a bearing disposed along said handle within said handle chamber, said bearing including said bearing surface and a passage at least partially defined by said bearing surface, said passage extending through said bearing receiving at least a portion of said connecting member.

11. An oral hygiene device according to claim 8, wherein said connecting member includes a connecting rod that extends between opposing first and second rod ends with said first rod end fixedly coupled to said vibratory source and said second end operatively connected to said cleaning head.

12. An oral hygiene device according to claim 8, wherein said mounting member is a directional mounting member that permits movement of said vibratory source along a principal plane of motion while substantially limiting movement of said vibratory source along a secondary plane of motion that is disposed approximately transverse to said principal plane of motion.

13. An oral hygiene device according to claim 12, wherein said movement of said vibratory source along said principal plane of motion travels through a first distance and said movement of said vibratory source along said secondary plane of motion travels through a second distance that is less than 25 percent of said first distance.

14. An oral hygiene device according to claim 12, wherein said first and second intermediate walls are disposed on opposing sides of said principal plane of motion such that said inner wall is suspended from said outer wall by said first and second intermediate walls.

15. An oral hygiene device according to claim 14, wherein said first and second intermediate walls of said mounting member extend lengthwise in approximate alignment with said secondary plane of motion.

16. A method of assembling an oral hygiene device, said method comprising:
   a) providing a handle that includes a longitudinal axis and a handle wall at least partially defining a handle cavity, said handle extending longitudinally between proximal and distal handle ends;
   b) providing a mounting member having a midplane and including an inner mounting wall, an outer mounting wall spaced radially outwardly from said inner mounting wall, and first and second intermediate walls having a length and extending lengthwise between and interconnecting said inner and outer mounting walls with said first intermediate wall disposed along one side of said midplane and said second intermediate wall disposed along the other side of said midplane;
   c) positioning said mounting member within said handle cavity in spaced relation to said distal end such that said midplane is disposed in approximate alignment with said axis and such that said first and second intermediate walls extend in said lengthwise direction transverse to said axis, and operatively connecting said outer side wall along said handle wall;
   d) providing a vibratory source, and operatively engaging said vibratory source and said inner side wall of said mounting member such that operation of said vibratory source can induce flexing of said first and second intermediate walls along said length thereof and result in vibratory movement of said inner mounting wall and said vibratory source relative to said outer mounting wall;

e) providing a bearing surface along said handle adjacent said distal end thereof;

f) providing a connecting member that extends longitudinally between first and second ends thereof, and operatively interconnecting said first end of said connecting member and said vibratory source such that said vibratory movement induced by said vibratory source can be communicated to said connecting member; and, g) supporting a cleaning head on said handle adjacent said distal end thereof such that at least a portion of said cleaning head is disposed along an opposing side of said bearing surface from said vibratory source, and operatively interconnecting said cleaning head and said second end of said connecting member such that said vibratory movement induced by said vibratory source when acting in a first direction along a plane of motion results in said cleaning head being displaced in an opposing second direction along said plane of motion.

17. A method according to claim 16, wherein said cleaning head has a desired principal plane of motion, said midplane of said mounting element is a symmetrical midplane, and said method further comprises rotationally orienting said mounting element about said longitudinal axis such that said symmetrical midplane of said mounting element is disposed in a predetermined angular orientation relative to said desired principal plane of motion of said cleaning head.

18. A method according to claim 17, wherein orienting said mounting element about said longitudinal axis includes orienting said mounting element such that said symmetrical midplane is disposed in approximate alignment with said desired principle plane of motion of said cleaning head.

19. A method according to claim 16, wherein providing a vibratory source in d) includes providing a rotary actuator and a vibratory mass, said rotary actuator including a rotatable output shaft, and said vibratory mass eccentrically mounted on said rotatable output shaft, and operatively engaging said vibratory source and said inner side wall of said mounting member in d) includes orienting said rotatable output shaft in approximate alignment with said axis.

20. A method according to claim 16 further comprising providing a pair of electrical contacts, securing said pair of electrical contacts on said handle, and placing said pair of electrical contacts in electrical communication with said vibratory source.

21. A method according to claim 20 further comprising providing an electrical switch, securing said electrical switch on said handle, and placing said the electrical switch in electrical communication between one of said electrical contacts and said vibratory source.

* * * * *